US012594224B2

(12) United States Patent
Daep et al.

(10) Patent No.: US 12,594,224 B2
(45) Date of Patent: *\*Apr. 7, 2026*

(54) ORAL CARE COMPOSITIONS AND METHODS OF USE

(71) Applicant: Colgate-Palmolive Company, New York, NY (US)

(72) Inventors: Carlo Daep, Brooklyn, NY (US); Rabab Ahmed, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 607 days.

This patent is subject to a terminal disclaimer.

(21) Appl. No.: 17/951,734

(22) Filed: Sep. 23, 2022

(65) Prior Publication Data

US 2023/0092135 A1      Mar. 23, 2023

Related U.S. Application Data

(60) Provisional application No. 63/247,638, filed on Sep. 23, 2021.

(51) Int. Cl.
| | |
|---|---|
| *A61K 8/43* | (2006.01) |
| *A61K 8/21* | (2006.01) |
| *A61K 8/27* | (2006.01) |
| *A61K 8/41* | (2006.01) |
| *A61Q 11/00* | (2006.01) |

(52) U.S. Cl.
CPC .................. *A61K 8/43* (2013.01); *A61K 8/21* (2013.01); *A61K 8/27* (2013.01); *A61K 8/416* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 9,486,396 | B2 | 11/2016 | Jaracz et al. |
| 10,058,493 | B2 | 8/2018 | Manus et al. |
| 10,342,750 | B2 | 7/2019 | Prencipe et al. |
| 10,441,517 | B2 | 10/2019 | Prencipe et al. |
| 10,617,620 | B2 | 4/2020 | Prencipe et al. |
| 10,744,077 | B2 | 8/2020 | Manus et al. |
| 2008/0038210 | A1* | 2/2008 | Yano ........................ A61K 8/39 |
| | | | 424/49 |
| 2009/0202454 | A1 | 8/2009 | Mello et al. |
| 2013/0071456 | A1 | 3/2013 | Fruge et al. |
| 2017/0020795 | A1 | 1/2017 | Maloney et al. |
| 2018/0015016 | A1 | 1/2018 | Huang et al. |
| 2018/0021234 | A1 | 1/2018 | Prencipe et al. |
| 2019/0201302 | A1 | 7/2019 | Uchino |
| 2019/0269586 | A1 | 9/2019 | Prencipe et al. |
| 2020/0009031 | A1 | 1/2020 | Prencipe et al. |
| 2020/0337959 | A1 | 10/2020 | Manus et al. |

FOREIGN PATENT DOCUMENTS

| | | |
|---|---|---|
| CA | 2478619 | 9/1999 |
| EP | 0368130 | 5/1990 |
| GB | 2210265 | 6/1989 |

OTHER PUBLICATIONS

International Search Report and the Written Opinion of the International Searching Authority issued in International Application PCT/US2022/044549 mailed Jan. 25, 2023.
Kim, Seong-Heun et al., "Antimicrobial drugs bearing guanidine moieties: A review", European Journal of Medicinal Chemistry, vol. 216, https://doi.org/10.1016/j.ejmech.2021.113293, Feb. 13, 2021 (Feb. 13, 2021), pp. 113293.

* cited by examiner

*Primary Examiner* — Nannette Holloman

(57) ABSTRACT
The disclosure relates to oral care compositions comprising guanidine in free or orally acceptable salt form, a cationic quaternary ammonium compound (e.g., a pyridinium compound) (e.g., cetyl pyridinium chloride (CPC)), a fluoride source, and optionally a zinc source (e.g., zinc lactate or zinc citrate and zinc oxide) as well as to methods of using and of making these compositions.

19 Claims, No Drawings

ORAL CARE COMPOSITIONS AND METHODS OF USE

RELATED APPLICATIONS

This application claims the benefit of U.S. Provisional Application No. 63/247,638, filed Sep. 23, 2021.

FIELD

The disclosure relates to oral care compositions comprising guanidine in free or orally acceptable salt form, a cationic quaternary ammonium compound (e.g., a pyridinium compound) (e.g., cetyl pyridinium chloride (CPC)), a fluoride source, and optionally a zinc source (e.g., zinc lactate or zinc citrate and zinc oxide) as well as to methods of using and of making these compositions.

BACKGROUND

Zinc is a well-known antimicrobial agent used in toothpaste compositions. At effective concentrations, zinc has been shown to inhibit bacterial glycolysis and the activity of bacterial proteases. Zinc is also a well-known essential mineral for human health, and has been reported to help strengthen dental enamel and to promote cell repair. Unfortunately, conventional toothpaste formulations often require a high concentration of zinc, e.g., 2% by weight or more, to achieve efficacy. At this concentration, the zinc imparts a notably astringent taste to the composition.

Antibacterial agents are commonly incorporated into oral care compositions to destroy or inhibit the growth of bacteria that may cause dental plaque, caries or dental decay, or bad breath. Many antibacterial agents are cationic in order to interact with the negatively-charged microbial cell membranes. Cetylpyridinium chloride (CPC) is a cationic quaternary ammonium compound used in oral care compositions. CPC is known to be effective in preventing dental plaque and reducing gingivitis. Generally, improvements in the delivery and efficacy of antibacterial agents would increase the efficacy and efficiency of oral care products.

There is thus a need for improved antibacterial oral care formulations that do not suffer from the drawbacks of conventional compositions.

BRIEF SUMMARY

Without being bound by theory the addition of guanidine in free or salt form could provide a way to efficiently deliver one or more antimicrobial agents, such as Cetylpyridinium chloride (CPC), to biofilms in the oral cavity.

Accordingly, the current formulations offer the advantage of robust microbial protection without significantly interfering with the stability of the oral care composition and by allowing for formulations which use less zinc and/or improve the delivery of zinc ions to biofilm in the oral cavity. Without being bound by any theory, it is believed that the presence of the guanidine may help to increase the delivery of CPC to enamel biofilm which can then an increased effect on inhibiting bacterial growth in the oral cavity of a user. Without being bound by theory, it is believed that guanidine can function as a chaotrophic agent that is capable of interfering in the electrostatic interaction among large molecules, e.g., proteins. Accordingly, without being bound by theory, guanidine possibly functions as a delivery agent for antimicrobial or antibacterial agents (e.g., cetylpyridinium chloride and/or zinc) by altering the physical properties of the biofilm EPS matrix resulting the destabilization and increased permeability of the matrix. In turn, again without being bound by theory, the resulting destabilization and increased permeability of the matrix is believed to allow for the uptake of large molecules, e.g., antibacterial agents.

Accordingly, it is believed that the incorporation of guanidine will result in an improvement in the delivery and efficacy of various antibacterial agents, e.g., CPC. Therefore, the addition of guanidine to oral care products is believed to improve various antibacterial performance and provide better biofilm and plaque control.

In one aspect the invention is an oral care composition (Composition 1.0) comprising:

a. guanidine, in free or salt form;

b. a cationic quaternary ammonium compound (e.g., a pyridinium compound) (e.g., cetyl pyridinium chloride (CPC));

c. a fluoride source (e.g., sodium fluoride)

For example, the invention contemplates any of the following compositions (unless otherwise indicated, values are given as percentage of the overall weight of the composition):

1.1 Composition 1.0 wherein the guanidine is in free form.

1.2 Composition 1.0, wherein the guanidine is in partial or whole salt form.

1.3 Any of the preceding compositions wherein the guanidine (e.g., Guanidine HCL) is present in an amount corresponding to 0.3% to 15%, (e.g., 0.4 wt. % to 3 wt. % of the total composition weight), (e.g., 0.3 wt. %-3 wt. % of the total composition weight) (e.g., about 0.44% by wt.), (e.g., about 0.45%), (e.g., about 0.9%), (e.g., about 1.5%), (e.g., about 1.8% by wt.).

1.4 Any of the preceding compositions wherein the guanidine is present from 0.1 wt. %-5.0 wt. %. (e.g., about 0.44%, 0.45%, 0.9%, or 1.8% by wt.).

1.5 Any of the preceding compositions wherein the guanidine is present in about 0.44 by wt. % of the total composition weight.

1.6 Any of the preceding compositions wherein the guanidine is present in about 0.45 by wt. % of the total composition weight.

1.7 Any of the preceding compositions wherein the guanidine is present in about 0.9% by wt. % of the total composition weight.

1.8 Any of the preceding compositions wherein the guanidine is present in about 1.5% by wt. % of the total composition weight.

1.9 Any of the preceding compositions wherein the guanidine is present in about 1.8 by wt. % of the total composition weight.

1.10 Any of the preceding compositions, wherein the guanidine is a salt selected from the group consisting of: Guanidine Hydrochloride (also referred to as guanidinium chloride), Guanidine Monohydrate, Guanidine Monohydrobromide, Guanidine Monohydrochloride, Guanidine Monohydroiodine, Guanidine Nitrate, Guanidine Phosphate, Guanidine Sulfate, and combinations thereof.

1.11 The preceding composition, wherein the guanidine salt is guanidine hydrochloride.

1.12 Any of the preceding compositions, wherein the guanidine is in the oral care compositions in the form of guanidinium (e.g., the conjugate acid).

1.13 Any of the preceding compositions wherein the guanidine ionized by neutralization with an acid or a salt of an acid.

1.14 Any of the preceding, wherein the weight of the guanidine refers to the weight of the salt (e.g., Guanidine HCL) relative to the total composition weight.

1.15 Any of preceding compositions wherein the composition is ethanol-free.

1.16 Any of the preceding compositions further comprising a fluoride source selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.17 Any of the preceding compositions, wherein the cationic quaternary ammonium compound comprises a pyridinium compound.

1.18 The preceding composition, wherein the pyridinium compound comprises cetylpyridinium chloride (CPC) (e.g., CPC in an amount from 0.05%-0.125% by wt. relative to the total composition).

1.19 The preceding composition, wherein the pyridinium compound comprises cetyl pyridinium chloride in an amount from 0.05%-0.125% by wt. relative to the total composition (e.g., about 0.075% by wt. relative to the total composition).

1.20 Any of the preceding compositions wherein the fluoride source is a fluorophosphate.

1.21 Any of the preceding compositions wherein the fluoride source is sodium monofluorophosphate.

1.22 Any of the preceding compositions wherein the fluoride source is sodium fluoride.

1.23 Any of the preceding compositions wherein the fluoride source is stannous fluoride.

1.24 Any of the preceding compositions wherein the fluoride source is a fluoride salt present in an amount of 0.1 wt. % to 2 wt. % (0.1 wt. %-0.6 wt. %) of the total composition weight (e.g., sodium fluoride (e.g., about 0.3 wt. %) or sodium monofluorophosphate).

1.25 Any of the preceding compositions wherein the fluoride source is a soluble fluoride salt which provides fluoride ion in an amount of from 50 to 25,000 ppm (e.g., 750-2000 ppm, e.g., 1000-1500 ppm, e.g., about 1000 ppm, e.g., about 1450 ppm)

1.26 Any of the preceding compositions wherein the fluoride source is sodium fluoride which provides fluoride in an amount from 750-2000 ppm (e.g., about 1450 ppm)

1.27 Any of the preceding compositions wherein the fluoride source is selected from sodium fluoride and sodium monofluorophosphate and which provides fluoride in an amount from 1000 ppm-1500 ppm.

1.28 Any of the preceding compositions wherein the fluoride source is sodium fluoride or sodium monofluorophosphate and which provides fluoride in an amount of about 1450 ppm.

1.29 Any of the preceding compositions wherein the pH is between 7.5 and 10.5, e.g., 9.0 to 10.0, e.g., 9.4.

1.30 Any of the preceding compositions further comprising calcium carbonate.

1.31 The composition of 1.30, wherein the calcium carbonate is a precipitated calcium carbonate high absorption (e.g., 20% to 30% by weight of the composition) (e.g., 25% precipitated calcium carbonate high absorption).

1.32 The composition of 1.31, further comprising a precipitated calcium carbonate—light (e.g., about 10% precipitated calcium carbonate—light) (e.g., about 10% natural calcium carbonate).

1.33 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophosphate, monosodium phosphate, pentapotassium triphosphate and mixtures of any of two or more of these, e.g., in an amount of 1-20%, e.g., 2-8%, e.g., ca. 5%>, by weight of the composition.

1.34 The composition of 1.33, wherein the stannous salt is selected from stannous fluoride, stannous pyrophosphate, and combinations thereof.

1.35 Any of the preceding compositions comprising tetrapotassium pyrophosphate, disodium hydrogenorthophosphate, monosodium phosphate, and pentapotassium triphosphate.

1.36 Any of the preceding compositions comprising a polyphosphate.

1.37 The composition of 1.36, wherein the polyphosphate is tetrasodium pyrophosphate.

1.38 The composition of 1.37, wherein the tetrasodium pyrophosphate is from 0.1-1.0 wt. % (e.g., about 0.5 wt. %).

1.39 Any of the preceding compositions further comprising an abrasive or particulate (e.g., silica).

1.40 Any of the preceding compositions wherein the silica is synthetic amorphous silica. (e.g., 1%-25% by wt.) (e.g., 8%-25% by wt.)

1.41 Any of the preceding composition wherein the silica abrasives are silica gels or precipitated amorphous silicas, e.g., silicas having an average particle size ranging from 2.5 microns to 12 microns.

1.42 Any of the preceding compositions further comprising a small particle silica having a median particle size (d50) of 1-5 microns (e.g., 3-4 microns) (e.g., about 5 wt. % Sorbosil AC43 from Ineos Silicas, Warrington, United Kingdom).

1.43 Any of the preceding compositions wherein 20-30 wt. % of the total silica in the composition is small particle silica (e.g., having a median particle size (d50) of 3-4 microns) and wherein the small particle silica is about 5 wt. % of the oral care composition.

1.44 Any of the preceding compositions comprising silica wherein the silica is used as a thickening agent, e.g., particle silica.

1.45 Any of the preceding compositions further comprising a nonionic surfactant, wherein the nonionic surfactant is in an amount of from 0.5-5%, e.g., 1-2%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof.

1.46 Any of the preceding compositions, wherein the poloxamer nonionic surfactant has a polyoxypropylene molecular mass of from 3000 to 5000 g/mol and a polyoxyethylene content of from 60 to 80 mol %, e.g., the poloxamer nonionic surfactant comprises poloxamer 407.

1.47 Any of the preceding compositions further comprising sorbitol, wherein the sorbitol is in a total amount of 10-40% (e.g., about 23%).

1.48 Any of the preceding compositions further comprising glycerin, wherein the glycerin is in a total amount of 5-20% (e.g., about 7.5%).

1.49 Any of the preceding compositions further comprising propylene glycol, wherein the propylene glycol is in a total amount of 5-20% (e.g., about 7%).

1.50 Any of the preceding compositions further comprising a zinc ion source.

1.51 The preceding composition, wherein the zinc ion source is selected from zinc citrate, zinc oxide, zinc sulfate, zinc silicate, zinc lactate, zinc phosphate, and combinations thereof.

1.52 The preceding composition, wherein the zinc ion source comprises zinc lactate (e.g., from 0.1%-2% by wt.) (e.g., about 0.28%).

1.53 The composition of 1.51, wherein the zinc ion source comprises zinc citrate and zinc oxide.

1.54 The preceding compositions, wherein the ratio of the amount of zinc oxide (e.g., wt. %) to zinc citrate (e.g., wt. %) is from 1.5:1 to 4.5:1 (e.g., 2:1, 2.5:1, 3:1, 3.5:1, or 4:1).

1.55 Any of the preceding compositions, wherein the zinc citrate is in an amount of from 0.25 to 0.75 wt. % (e.g., 0.5 wt. %) and zinc oxide may be present in an amount of from 0.75 to 1.25 wt. % (e.g., 1.0 wt. %) based on the weight of the oral care composition.

1.56 Any of the preceding compositions wherein the zinc citrate is about 0.5 wt. %.

1.57 Any of the preceding compositions wherein the zinc oxide is about 1.0 wt. %.

1.58 Any of the preceding compositions where the zinc citrate is about 0.5 wt. % and the zinc oxide is about 1.0 wt. %.

1.59 Any of the preceding compositions further comprising a preservative selected from: benzyl alcohol, Methylisothizolinone ("MIT"), Sodium bicarbonate, sodium methyl cocoyl taurate (tauranol), lauryl alcohol, and polyphosphate.

1.60 The composition of 1.59, wherein the benzyl alcohol is present from 0.1-0.6 wt. %, (e.g., 0.1-0.4 wt. %) e.g., about 0.1 wt. %, about 0.2 wt. %, or about 0.3 wt. %.

1.61 The composition of 1.60, wherein the benzyl alcohol is about 0.1 wt. %.

1.62 Any of the preceding compositions comprising polymer films.

1.63 Any of the preceding compositions comprising flavoring, fragrance and/or coloring.

1.64 The composition of 1.63, wherein the flavoring agent is sodium saccharin, sucralose, or a mixture thereof.

1.65 Any of the preceding compositions, wherein the composition comprises a thickening agents selected from the group consisting of carboxyvinyl polymers, carrageenan, hydroxyethyl cellulose and water soluble salts of cellulose ethers (e.g., sodium carboxymethyl cellulose and sodium carboxymethyl hydroxyethyl cellulose).

1.66 Any of the preceding compositions, wherein the compositions comprises sodium carboxymethyl cellulose (e.g., from 0.5 wt. %-1.5 wt. %)

1.67 Any of the preceding compositions comprising from 5%-85%, e.g., 10%-85%, e.g., 20%-85%, e.g., 30%-85%, e.g., 40%-85%, e.g., 50%-85%, e.g., 60%-85%, e.g., 70%-85%, e.g., 75%-85%, e.g., about 10%, e.g., about 20%, e.g., about 30%, e.g., about 40%, e.g., about 50%, e.g., about 60%, e.g., about 70%, e.g., about 80%.

1.68 Any of the preceding compositions comprising an additional antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc chloride, zinc lactate, zinc sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.69 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

1.70 Any of the preceding compositions comprising a whitening agent.

1.71 Any of the preceding compositions comprising a whitening agent selected from a whitening active selected from the group consisting of peroxides, metal chlorites, perborates, percarbonates, peroxyacids, hypochlorites, and combinations thereof.

1.72 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.73 Any of the preceding compositions further comprising an agent that interferes with or prevents bacterial attachment, e.g., ELA or chitosan.

1.74 Any of the preceding compositions further comprising a basic amino acid.

1.75 The composition of 1.74, wherein the basic amino acid is selected from: arginine, lysine, serine, citrullene, ornithine, creatine, histidine, diaminobutanoic acid, diaminoproprionic acid, salts thereof or combinations thereof, e.g., wherein the basic amino acid is arginine in free or salt form. 1.76 Any of the preceding composition, wherein the oral care composition is a dentifrice comprising a zwitterionic surfactant, for example a betaine surfactant, for example cocamidopropylbetaine, e.g., in an amount of from about 0.1% to about 4.5% by weight, e.g., 0.5-2% cocamidopropylbetaine by weight of the composition 1.77 Any of the preceding compositions comprising:
  a. about 0.2%-2.5% guanidine (e.g., guanidine HCl) by wt. of the total composition (e.g., about 0.44%)
  b. cetylpyridinium chloride (CPC) from 0.05%-0.125% by wt. relative to the total composition (e.g., CPC in an amount of about 0.075% by wt. relative to the total composition)
  c. from 0.1%-0.5% sodium fluoride.
1.78 Any of the preceding compositions comprising:
  a. about 0.2%-2.5% guanidine (e.g., guanidine HCl) by wt. of the total composition (e.g., about 0.44%)
  b. cetylpyridinium chloride (CPC) from 0.05%-0.125% by wt. relative to the total composition (e.g., CPC in an amount of about 0.075% by wt. relative to the total composition)
  c. from 0.1%-0.5% sodium fluoride.
  d. from 0.75%-1.25% zinc oxide (e.g., about 1.0% zinc oxide)
  e. from 0.25%-0.75% zinc citrate (e.g., about 0.5% zinc citrate).
1.79 Any of the preceding compositions comprising:
  a. about 0.2%-2.5% guanidine (e.g., guanidine HCl) by wt. of the total composition (e.g., about 0.44%)
  b. cetylpyridinium chloride (CPC) from 0.05%-0.125% by wt. relative to the total composition (e.g., CPC in an amount of about 0.075% by wt. relative to the total composition)
  c. from 0.1%-0.5% sodium fluoride.
  d. from 0.75%-1.25% zinc oxide (e.g., about 1.0% zinc oxide)
  e. from 0.25%-0.75% zinc citrate (e.g., about 0.5% zinc citrate)
  f. from 0.5%-5% arginine (e.g., 1.5% L-arginine).
1.80 Any of foregoing compositions comprising:
  a. about 0.2%-2.5% guanidine (e.g., guanidine HCl) by wt. of the total composition (e.g., about 0.44%)
  b. cetylpyridinium chloride (CPC) from 0.05%-0.125% by wt. relative to the total composition (e.g., CPC in an amount of about 0.075% by wt. relative to the total composition)
  c. from 0.1%-0.5% sodium fluoride by wt. of the total composition
  d. from 0.1%-1.0% of zinc lactate by wt. of the total composition (e.g., about 0.22%).
1.81 Any of the foregoing compositions comprising:
  a. about 0.2%-2.5% guanidine (e.g., guanidine HCl) by wt. of the total composition (e.g., about 0.44%)
  b. cetylpyridinium chloride (CPC) from 0.05%-0.125% by wt. relative to the total composition (e.g., CPC in an amount of about 0.075% by wt. relative to the total composition)
  c. from 0.1%-0.5% sodium fluoride by wt. of the total composition
  d. from 0.1%-1.0% of zinc lactate by wt. of the total composition (e.g., about 0.22%)
  e. from 0.5%-5% arginine (e.g., 1.5% L-arginine).
1.82 Any of the preceding compositions wherein the composition is in the form of a toothpaste or a mouthwash, and the guanidine is guanidine hydrochloride in an amount of 0.4-0.5% by weight.
1.83 Any of the preceding compositions wherein the composition is in the form of a toothpaste comprising
  0.5-1.5 wt. % zinc lactate,
  0.05- to 0.1 wt. % CPC,
  0.4-0.5 wt. % guanidine HCl, and
  1400-1500 ppm sodium fluoride.

1.84 Any of the preceding compositions wherein the composition is in the form of a toothpaste comprising
  0.5-1.5 wt. % zinc lactate,
  0.05- to 0.1 wt. % CPC,
  0.4-0.5 wt. % guanidine HCl, and
  1400-1500 ppm sodium fluoride.
1.85 Any of the preceding compositions wherein the composition is in the form of a mouthwash comprising 0.05- to 0.1 wt. % CPC, 0.2-0.3 wt. % zinc lactate, and 0.4-0.5 wt. % guanidine HCl.
1.86 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) inhibit microbial biofilm formation in the oral cavity, (ix) raise and/or maintain plaque pH at levels of at least pH 5.5 following sugar challenge, (x) reduce plaque accumulation, (xi) treat, relieve or reduce dry mouth, (xii) clean the teeth and oral cavity (xiii) reduce erosion, (xiv) prevents stains and/or whiten teeth, (xv) immunize the teeth against cariogenic bacteria; and/or (xvi) promote systemic health, including cardiovascular health, e.g., by reducing potential for systemic infection via the oral tissues.
1.87 Any of the preceding oral compositions, wherein the oral composition may be any of the following oral compositions selected from the group consisting of: a toothpaste or a dentifrice, a mouthwash or a mouth rinse, a topical oral gel, and a denture cleanser.
1.88 A composition obtained or obtainable by combining the ingredients as set forth in any of the preceding compositions.
1.89 A composition of any of the preceding compositions further comprising an amino acid (e.g., arginine)
1.90 A composition of any of the preceding compositions, wherein the guanidine is in free or orally acceptable salt form and is not present as a moiety in one or more larger organic molecules.
1.91 The preceding composition, wherein guanidine is present in free or orally acceptable salt form and the composition does not comprise an amino acid (e.g., arginine).
1.92 The preceding composition, wherein the composition does not comprise arginine.
1.93 A composition obtained or obtainable by combining the ingredients as set forth in any of the preceding compositions.
1.94 A composition for use as set for in any of the preceding compositions.
1.95 Any foregoing composition wherein, upon application of the composition to the teeth, the guanidine in free or salt form enhances the antibacterial efficacy of the cationic quaternary ammonium compound (e.g., CPC) by enhancing its delivery to bacterial biofilms.

In another embodiment, the invention encompasses a method to improve oral health comprising applying an effective amount of the oral composition of any of Composition 1.0 et seq set forth above to the oral cavity of a subject in need thereof, e.g., a method to i. reduce or inhibit formation of dental caries, ii. reduce, repair or inhibit early enamel lesions, e.g., as detected by quantitative light-induced fluorescence (QLF) or electrical caries measurement (ECM), iii. reduce or inhibit demineralization and promote remineralization of the teeth, iv. reduce hypersensitivity of the teeth, v. reduce or inhibit gingivitis, vi. promote healing of sores or cuts in the mouth, vii. reduce levels of acid producing bacteria, viii. inhibit microbial bio film formation in the oral cavity, ix. raise and/or maintain plaque pH at levels of at least pH 5.5 following sugar challenge, x. reduce plaque accumulation, xi. treat dry mouth, xii. enhance systemic health, including cardiovascular health, e.g., by reducing potential for systemic infection via the oral tissues, xiii. Whiten teeth, xiv. reduce erosion of the teeth, xv. immunize (or protect) the teeth against cariogenic bacteria and their effects, and/or xvi. clean the teeth and oral cavity.

The invention further comprises the use of sodium bicarbonate, sodium methyl cocoyl taurate (tauranol), MIT, and benzyl alcohol and combinations thereof in the manufacture of a Composition of the Invention, e.g., for use in any of the indications set forth in the above method of Composition 1.0, et seq.

DETAILED DESCRIPTION

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

As used herein, the term "guanidine" refers to the compound with the formula $HNC(NH_2)_2$ in free or salt form. The conjugate acid of guanidine is the guanidinium cation, $(C(NH_2)^+_3)$. Derivatives of guanidine may exist as salts which contain the conjugate acid. Guanidine is a very strong base in water. In neutral water, one of skill in the art will understand that guanidine will most likely exist as guanidinium. One of skill in the art will understand the circumstances when guanidine exists in the formulation in the protonated guanidinium form. "Guanidine", as used herein, can refer to, for example, to guanidine or guanidinium, or a salt thereof. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art.

As used herein, an "oral care composition" refers to a composition for which the intended use includes oral care, oral hygiene, and/or oral appearance, or for which the intended method of use comprises administration to the oral cavity, and refers to compositions that are palatable and safe for topical administration to the oral cavity, and for providing a benefit to the teeth and/or oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice. As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

Amino Acid

In some aspects, any of Compositions 1.0 et seq can include a basic or neutral amino acid. The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

For example, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

In another aspect, the compositions of the invention (e.g., any of Compositions 1.0 et seq) can include a neutral amino acid, which can include, but are not limited to, one or more neutral amino acids selected from the group consisting of alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, and combinations thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source

The oral care compositions include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium mono-fluorophosphate, rather than merely ionically bound, e.g., as in sodium fluoride.

Surfactants

The invention may in some embodiments contain anionic surfactants, e.g., the Compositions of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphe-noxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

In still another embodiment amphoteric surfactants can be used. Suitable amphoteric surfactants, without limitation, are derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01 weight % to 10 weight %, for example, from 0.05 weight % to 5 weight % or from 0.1 weight % to 2 weight % by total weight of the composition.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trial-kali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.5 wt. % pyrophosphate ions, 0.9-3 wt. %. The pyrophosphates also contribute to preservation of the compositions by lowering water activity.

Polymers

The oral care compositions of the invention also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g., about 5.5 microns. For example a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g., 2.2-2.6 microns, e.g., about 2.4 microns, and a D10 of 1-2 microns, e.g., 1.2-1.4, e.g., about 1.3 microns. The particles have relatively high water absorption, e.g., at least 25 g/100 g, e.g., 30-70 g/100 g. Examples of commercially available products suitable for use in the present invention include, for example, Carbolag® 15 Plus from Lagos Industria Quimica.

In certain embodiments the any of the oral care composition of the disclosure (e.g., any of Composition 1.0 et seq) may comprise additional calcium-containing abrasives, for example calcium phosphate abrasive, e.g., tricalcium phosphate $(Ca_3(PO_4)_2)$, hydroxyapatite $(Ca_{10}(PO_4)_6(OH)_2)$, or dicalcium phosphate dihydrate $(CaHPO_4 \cdot 2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example synthetic amorphous silica. Silica may also be available as a thickening agent, e.g., particle silica. For example, the silica can also be small particle silica (e.g., Sorbosil AC43 from Ineos Silicas, Warrington, United Kingdom). However the additional abrasives are preferably not present in a type or amount so as to increase the RDA of the dentifrice to levels which could damage sensitive teeth, e.g., greater than 130.

Enzymes

The oral care compositions of the disclosure (e.g., any of Compositions 1.0 et seq) may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water

Water is present in the oral compositions of the invention. Water, employed in the preparation of commercial oral compositions should be deionized and free of organic impurities. Water commonly makes up the balance of the compositions and in certain aspects of any of the oral care compositions of the disclosure (e.g., any of Composition 1.0 et seq), includes: 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

In certain aspects the oral care compositions of the disclosure (e.g., any of Composition 1.0 et seq), comprise a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerin and sorbitol may be used in certain embodiments as the humectant component of the compositions herein.

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6-month treatments are made. In addition, a classical caries score for root surfaces is made using a tactile probe. The hardness is classified on a three-point scale: hard, leathery, or soft. In this type of study, typically the results are reported as electrical resistance (higher number is better) for the ECM measurements and an improvement in hardness of the lesion based on the tactile probe score.

Test methods for the desensitizing properties of the compositions described herein, uses the method described in U.S. Pat. No. 5,589,159, the disclosure of which is incorporated by reference herein in its entirety. This method measures the hydraulic conductance of materials, providing an objective reduction in fluid flow that correlates with reduction in fluid flow in dentinal tubules. In this method, intact human molars free from caries and restorations are sectioned perpendicularly to the long axis of the tooth with a metallurgical saw to form thin sections, or discs, from about 0.4 to about 0.8 mm thick. Sections containing dentin and free of enamel were selected for testing and then etched with citric acid solution to remove the smear layer. Each disc was mounted into a split chambered device described in J. Dent. Research, 57: 187 (1978) which is a special leak-proof chamber connected to a pressurized fluid reservoir containing a tissue culture fluid. By using a mixture of pressurized nitrogen and carbon dioxide gas, the fluid can be made at physiological pH. To further ensure accuracy, the discs were wetted with artificial saliva (phosphate buffer saline, PBS) to approximate intra-oral conditions. The apparatus includes a glass capillary tube attached to a flow sensor (FLODEC, DeMarco Engineering SA, Geneva). An air bubble is injected into the glass capillary tube. By measuring the displacement of the bubble as a function of time, fluid flow through the dentin disc can be measured. Fluid flow is equivalent to the dentin permeability.

The Compositions of the Invention are thus useful in a method to reduce early lesions of the enamel (as measured by QLF or ECM) relative to a composition lacking effective amounts of fluorine and/or arginine.

The Compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least pH 5.5 following sugar challenge, reduce plaque accumulation, and/or clean the teeth and oral cavity.

Finally, by increasing the pH in the mouth and discouraging pathogenic bacteria, the Compositions of the Invention are useful to promote healing of sores or cuts in the mouth.

The compositions and methods according to the invention (e.g., Composition 1.0 et seq) can be incorporated into oral compositions for the care of the mouth and teeth such as toothpastes, transparent pastes, gels, mouth rinses, sprays and chewing gum.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to *Heliobacter*, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

CPC Delivery and Biofilm Viability—Test 1

Saliva-derived biofilms are cultured on HAP disk at 37 C under 5% CO2. The biofilms are cultured in McBain media supplemented with hemin and vitamin K for a total of ~60 hours. The media are replaced twice daily (~12 hour intervals). The resulting biofilm culture is treated once with mouthwash samples (table below) for 2 minutes under agitation (80 rpm). The biofilms are washed twice at 5 minute intervals under agitation (80 rpm). Following treatment, the biofilms are allowed to recover for 3 hours in sterile dH2O at 37 C prior to biofilm harvesting by sonication to dislodge and suspend the bacteria. The collected bacteria are assessed for total biomass via Syto9 staining and viability using Baclight Bacterial Viability Kit (Promega) to quantify approximate ATP (expressed as relative luminescence units; RLU) content in the biofilms. Bacterial viability is normalized based Syto9 staining of the biofilm samples.

TABLE 1

| Mouthwash samples - CPC Delivery | | | |
|---|---|---|---|
| Mouthwash comprising (wt. %): | Formula Designation | CPC Delivered (ppm) | StErr |
| Untreated | Control 1 (negative control) | 0 | 0 |
| 0.075% CPC | Control 2 (positive control) | 1.68 | 0.49 |
| 0.075% CPC, 0.44% Guanidine | Formula A | 1.82 | 0.66 |

The mouthwashes are evaluated for CPC delivery in biofilm, as well as bacterial ATP which serve as a measure of viability, i.e., lower levels of ATP indicate that viable biofilm are decreased. Importantly, the data in Table 1 demonstrates an increase in CPC delivery with the addition of guanidine. The results in Table 2 demonstrate that the addition of guanidine also decreases the amount of viable biofilm in vitro:

TABLE 2

| Mouthwash comprising (wt. %): | Formula Designation | Biofilm viability (ATP:RLU) | StErr | % Reduction vs. CPC |
|---|---|---|---|---|
| Untreated | Control 1 (negative control) | 3,292,313 | 828,678.6 | N/A |
| 0.075% CPC | Control 2 (positive control) | 3,182,740 | 482,953.2 | 0 |
| 0.075% CPC, 0.44% Guanidine | Formula A | 2,485,047 | 482,953.2 | 21.9% |

From Table 2 increase in CPC delivery is inversely related to bacterial viability with a reduction in ATP levels as the guanidine concentration increase. Without being bound by theory, this data suggests that guanidine may be capable in enhancing the antibacterial efficacy of CPC by driving an improvement in CPC delivery in the biofilms.

Example 2

CPC Delivery and Biofilm Viability—Test 2

Saliva-derived biofilms are cultured on HAP disk at 37 C under 5% CO2. The biofilms are cultured in McBain media supplemented with hemin and vitamin K for a total of ~60 hours. The media are replaced twice daily (~12 hour intervals). The resulting biofilm culture is treated once with mouthwash slurries (table below) for 2 minutes under agitation (80 rpm). The biofilms are washed twice at 5 minute intervals under agitation (80 rpm). Following treatment, the biofilms are allowed to recover for 3 hours in sterile dH2O at 37 C prior to biofilm harvesting by sonication to dislodge and suspend the bacteria. The collected bacteria are assessed for total biomass via Syto9 staining and viability using Baclight Bacterial Viability Kit (Promega) to quantify approximate ATP (expressed as relative luminescence units; RLU) content in the biofilms. Bacterial viability is normalized based Syto9 staining of the biofilm samples.

TABLE 3

Mouthwash samples - CPC Delivery

| Mouthwash comprising (wt. %): | Formula Designation | CPC Delivered (ppm) | StErr |
|---|---|---|---|
| Untreated | Control 3 (negative control) | 0 | 0 |
| 0.075% CPC | Control 4 (positive control) | 1.99 | 0.38 |
| 0.075% CPC, 0.28% zinc lactate, 0.44% Guanidine | Formula B | 2.14 | 0.24 |

The mouthwashes are evaluated for CPC delivery in biofilm, as well as bacterial ATP which serve as a measure of viability, i.e., lower levels of ATP indicate that viable biofilm are decreased. Importantly, the data in Table 3 demonstrates an increase in CPC delivery with the addition of guanidine and zinc lactate. The results in Table 2 demonstrate that the addition of guanidine also decreases the amount of viable biofilm in vitro:

TABLE 4

| Mouthwash comprising (wt. %): | Formula Designation | Biofilm viability (ATP:RLU) | StErr | % Reduction vs. CPC |
|---|---|---|---|---|
| Untreated | Control 1 (negative control) | 3,292,313 | 828,678.6 | N/A |
| 0.075% CPC | Control 2 (positive control) | 3,247,687 | 973,586.8 | 0 |
| 0.075% CPC, 0.28% zinc lactate, 0.44% Guanidine | Formula A | 2,467,033 | 703,983 | 24% |

From Table 4 increase in CPC delivery is inversely related to bacterial viability with a reduction in ATP levels as the guanidine concentration increase. Without being bound by theory, this data again suggests that guanidine may be capable in enhancing the antibacterial efficacy of CPC by driving an improvement in CPC delivery in the biofilms. Moreover, without being bound by theory, the addition of zinc lactate may further reduce the amount of viable biofilm in vitro.

Example 3

Mouthwash Formulas used in above Tables 1~4 are as follows:
(*All ingredients listed by wt. % relative to the total composition)

| Ingredients | Control 2 | Formula A | Control 4 | Formula B |
|---|---|---|---|---|
| Demineralized Water | q. s. | q. s. | q. s. | q. s. |
| Nonionic Surfactant | 0.4 | 0.4 | 0.4 | 0.4 |
| Color, Flavoring and Sweeteners | 0.1735 | 0.1735 | 0.1735 | 0.1735 |

-continued

| Ingredients | Control 2 | Formula A | Control 4 | Formula B |
|---|---|---|---|---|
| Cetylpyridinium Chloride | 0.0750 | 0.0750 | 0.0750 | 0.075 |
| Preservative | 0.1 | 0.1 | 0.1 | 0.1 |
| 99.5% Vegetable Refined Glycerin | 7.5 | 7.5 | 7.5 | 7.5 |
| Non-Crystal Sorbitol | 5.5 | 5.5 | 5.5 | 5.5 |
| Propylene glycol | 7 | 7 | 7 | 7 |
| Alkali Phosphate Salt | 0.1 | 0.1 | — | — |
| pH Adjuster | 0.1 | 0.01 | 0.05 | 0.05 |
| Sodium Fluoride | 0.05 | 0.05 | 0.05 | 0.05 |
| Guanidine HCl | — | 0.44 | — | 0.44 |
| Zinc Lactate Dihydrate | — | — | 0.28 | 0.28 |
| Total | 100 | 100 | 100 | 100 |

Example 4

In one representative formulation, a dentifrice will comprise the following:
a. About 1.0 wt. % zinc lactate
b. 0.075 wt. % CPC
c. About 0.45 wt. % guanidine HCL
d. About 1450 ppm sodium fluoride; and water.
In one representative formulation, a dentifrice will comprise the following:

a. 0.075 wt. % CPC
b. About 0.45 wt. % guanidine HCL
c. About 1450 ppm sodium fluoride; and water.
Wherein the dentifrices are expected to enhance CPC delivery into biofilms, relative to certain CPC containing formulations without guanidine, and improve the antibacterial efficacy of CPC.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight of the entire composition. The amounts given are based on the active weight of the material.

While the present invention has been described with reference to embodiments, it will be understood by those skilled in the art that various modifications and variations may be made therein without departing from the scope of the present invention as defined by the appended claims.

The invention claimed is:

1. An oral care composition comprising:

a. guanidine, in free or orally acceptable salt form;

b. a cationic quaternary ammonium compound; and c. a fluoride source;

wherein the guanidine is selected from the group consisting of: guanidine hydrochloride, guanidine monohydrate, guanidine monohydrobromide, guanidine monohydrochloride, guanidine monohydroiodine, guanidine nitrate, guanidine phosphate, guanidine sulfate, and combinations thereof; and wherein the guanidine in free or salt form enhances delivery of the cationic quaternary ammonium compound to bacterial biofilms.

2. The oral care composition of claim 1, wherein the guanidine is in free form.

3. The oral care composition of claim 1, wherein the guanidine is in partial or whole salt form.

4. The oral care composition of claim 1, wherein the guanidine is present in an amount corresponding to 0.3% to 15% by wt. of the total composition weight.

5. The oral care composition of claim 1, wherein the guanidine is present from 0.1 wt. %-5.0 by wt. % of the total composition weight.

6. The oral care composition of claim 1, wherein the guanidine is present in an amount of about 0.45 by wt. % of the total composition weight.

7. The oral care composition of claim 1, wherein the guanidine is in the oral care compositions in the form of a guanidinium salt.

8. The oral care composition of claim 1, wherein the fluoride source is selected from: stannous fluoride, sodium fluoride, potassium fluoride, sodium monofluorophosphate, sodium fluorosilicate, ammonium fluorosilicate, amine fluoride, ammonium fluoride, titanium fluoride, hexafluorosulfate, and combinations thereof.

9. The oral care composition of claim 8, wherein the fluoride source is sodium fluoride.

10. The oral composition of claim 1, wherein the composition further comprises a zinc ion source.

11. The oral care composition of claim 10, wherein the zinc ion source is selected from zinc citrate, zinc oxide, zinc sulfate, zinc silicate, zinc lactate, zinc phosphate, and combinations thereof.

12. The oral care composition of claim 11, wherein the zinc ion source comprises zinc lactate.

13. The oral care composition of claim 11, wherein the zinc ion source comprises zinc citrate and zinc oxide.

14. The oral care composition of claim 13, wherein the ratio by weight of the amount of zinc oxide to zinc citrate is from 1.5:1 to 4.5:1.

15. The oral care composition of claim 14, wherein the zinc citrate is in an amount of from 0.25 to 0.75 wt. % and zinc oxide may be present in an amount of from 0.75 to 1.25 wt. % based on the weight of the oral care composition.

16. The oral care composition of claim 1, wherein the oral composition may be any of the following oral compositions selected from the group consisting of: a toothpaste or a dentifrice, a mouthwash or a mouth rinse, a topical oral gel, and a denture cleanser.

17. The oral care composition of claim 1, wherein the composition is in the form of a mouthwash comprising 0.05- to 0.1 wt. % CPC, 0.2-0.3 wt. % zinc lactate, and 0.4-0.5 wt. % guanidine HCl.

18. The oral care composition of claim 1, wherein the composition is obtained or obtainable by combining the ingredients as set forth in claim 1.

19. A method to improve oral health comprising applying an effective amount of the oral composition of claim 1 to the oral cavity of a subject in need thereof, wherein the method is effective to:

i. reduce or inhibit formation of dental caries, ii. reduce, repair or inhibit early enamel lesions, iii. reduce or inhibit demineralization and promote remineralization of the teeth, iv. reduce hypersensitivity of the teeth, v. reduce or inhibit gingivitis, vi. promote healing of sores or cuts in the mouth, vii. reduce levels of acid producing bacteria, viii. to increase relative levels of arginolytic bacteria, ix. inhibit microbial bio film formation in the oral cavity, x. raise and/or maintain plaque pH at levels of at least pH 5.5 following sugar challenge, xi. reduce plaque accumulation, xii. treat dry mouth, xiii. enhance systemic health, including cardiovascular health, xiv. whiten teeth, xv. reduce erosion of the teeth, xvi. immunize (or protect) the teeth against cariogenic bacteria and their effects, and/or xvii. clean the teeth and oral cavity.

\* \* \* \* \*